United States Patent
Rangisetty et al.

(10) Patent No.: US 9,624,258 B2
(45) Date of Patent: Apr. 18, 2017

(54) POLYMORPH OF REGADENOSON

(71) Applicant: Biophore India Pharmaceuticals PVT. Ltd., Hyderabad (IN)

(72) Inventors: Jagadeesh Babu Rangisetty, Hyderabad (IN); Manik Reddy Pullagurla, Hyderabad (IN); Mecheril Valsan Nandakumar, Hyderabad (IN); Dokula Neelam Naidu, Hyderabad (IN)

(73) Assignee: Biophore India Pharmaceuticals PVT. Ltd., Balanagar, Hyderabad (IN)

( * ) Notice: Subject to any disclaimer, the term of this patent is extended or adjusted under 35 U.S.C. 154(b) by 0 days.

(21) Appl. No.: 14/894,343

(22) PCT Filed: May 28, 2014

(86) PCT No.: PCT/IN2014/000360
§ 371 (c)(1),
(2) Date: Nov. 26, 2015

(87) PCT Pub. No.: WO2014/207758
PCT Pub. Date: Dec. 31, 2014

(65) Prior Publication Data
US 2016/0115191 A1  Apr. 28, 2016

(30) Foreign Application Priority Data
May 30, 2013  (IN) .......................... 2262/CHE/2013

(51) Int. Cl.
*C07H 19/00* (2006.01)
*C07H 19/16* (2006.01)
*C07H 19/167* (2006.01)

(52) U.S. Cl.
CPC ........... *C07H 19/16* (2013.01); *C07H 19/167* (2013.01); *C07B 2200/13* (2013.01)

(58) Field of Classification Search
None
See application file for complete search history.

(56) References Cited

U.S. PATENT DOCUMENTS 8,268,988 B2 *  9/2012  Zablocki .............. C07H 19/167
                                                        536/27.11
2011/0065931 A1   3/2011  Murthy et al.

FOREIGN PATENT DOCUMENTS

WO   WO2011123518 A1   10/2011
WO   WO2012027695 A1    3/2012

* cited by examiner

*Primary Examiner* — Patrick Lewis
(74) *Attorney, Agent, or Firm* — Ling Wu; Stephen Yang; Ling and Yang Intellectual Property

(57) ABSTRACT

The invention provides a novel polymorph of Regadenoson. More particularly, the invention provides propylene glycol solvate of Regadenoson. The invention also provides a process for the preparation of propylene glycol solvate of Regadenoson.

6 Claims, 2 Drawing Sheets

POLYMORPH OF REGADENOSON

FIELD OF INVENTION

The invention relates to novel polymorph of Regadenoson. More particularly, the invention relates to novel propylene glycol solvate of Regadenoson. The invention also relates to a process for preparing such novel polymorph.

BACKGROUND OF THE INVENTION

Regadenoson is an $A_{2A}$ adenosine receptor agonist that is a coronary vasodilator. It produces maximal hyperemia quickly and maintains it for an optimal duration that is practical for radionuclide myocardial perfusion imaging.

It was approved by the United States Food Drug Administration on Apr. 10, 2008 and is marketed by Astellas Pharma under the tradename Lexican. It has now gained approval in the European Union and is being sold in both the United Kingdom and Germany.

Regadenoson has a 2- to 3-minute biological half-life, as compared with adenosine's 30-second half-life. Regadenoson stress protocols using a single bolus have been developed, obviating the need for an intravenous line. Regadenoson stress tests are not affected by the presence of beta blockers, as regadenoson vasodilates but do not stimulate beta adrenergic receptors.

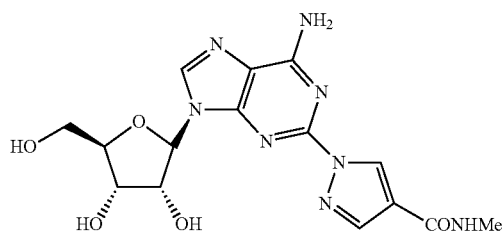

Formula I

The following patents and applications describe the synthesis of Formula I

A class of compounds possessing these desirable properties was disclosed in U.S. Pat. No. 6,403,567, the complete disclosure of which is hereby incorporated by reference. In particular, one compound disclosed in this patent, (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide, has been shown to be a highly selective $A_{2A}$ adenosine receptor agonist, and is presently undergoing clinical trials as a coronary vasodilator useful in cardiac imaging.

WO2008/143667 A1 provides the convenient synthesis for the large scale preparation of (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide, and polymorphs thereof, preferably as its monohydrate. Accordingly, in a first aspect, the invention relates to the preparation of a formula I.

Given the heightened interests in this compound, it has become desirable to find new methods of synthesis that provide a convenient method for making large quantities of the material in good yield and high purity. The patent (U.S. Pat. No. 6,403,567) provides several methods for preparing the compound. Although these methods are suitable for small scale syntheses, all synthetic methods disclosed in the patent utilize protecting groups, which is undesirable for large scale synthesis.

A novel process for preparation of Regadenoson has also been disclosed in applicant's Indian Patent Application No. 4486/CHE/2012 and the corresponding PCT application No. PCT/IN2013/000654 which is incorporated herein by reference.

U.S. Pat. No. 8,106,183B2 describes four polymorphs of Regadenoson and reports Regadenoson Monohydrate as a stable polymorph.

WO2012149196A1 describes a polymorph Form-D of Regadenoson.

IN 2011MU01470 describes several hydrated forms of Regadenoson and also reports anhydrous form.

Still there is a need for a highly pure form of Regadenoson for preparation of pharmaceutical formulations.

OBJECTS OF THE INVENTION

The primary object of the invention is to provide a novel polymorph of Regadenoson.

Another object of the invention is to provide novel propylene glycol solvate of Regadenoson.

A further object of the invention is to provide a process for the preparation of novel propylene glycol solvate of Regadenoson.

SUMMARY OF THE INVENTION

Accordingly, there is provided novel propylene glycol solvate of Regadenoson characterized by X-ray powder diffraction spectrum having principal peaks at 9.1, 18.0, 22.8 and 25.5 degrees 2 theta (2θ), as illustrated in FIG. 1.

There is also provide a process for the preparation of propylene glycol solvate of Regadenoson comprising the steps of:

a) dissolving crude Regadenoson in propylene glycol;
b) heating the mass to 75-80° C. to obtain clear solution;
c) cooling the solution to 20-25° C.;
d) optionally adding an anti-solvent to the solution;
e) filtering the solid that separated out;

The anti solvent employed in the process may be selected from THF, acetone, acetonitrile, toluene, ketones or alcohols.

DETAILED DESCRIPTION OF THE INVENTION

Figure 1:
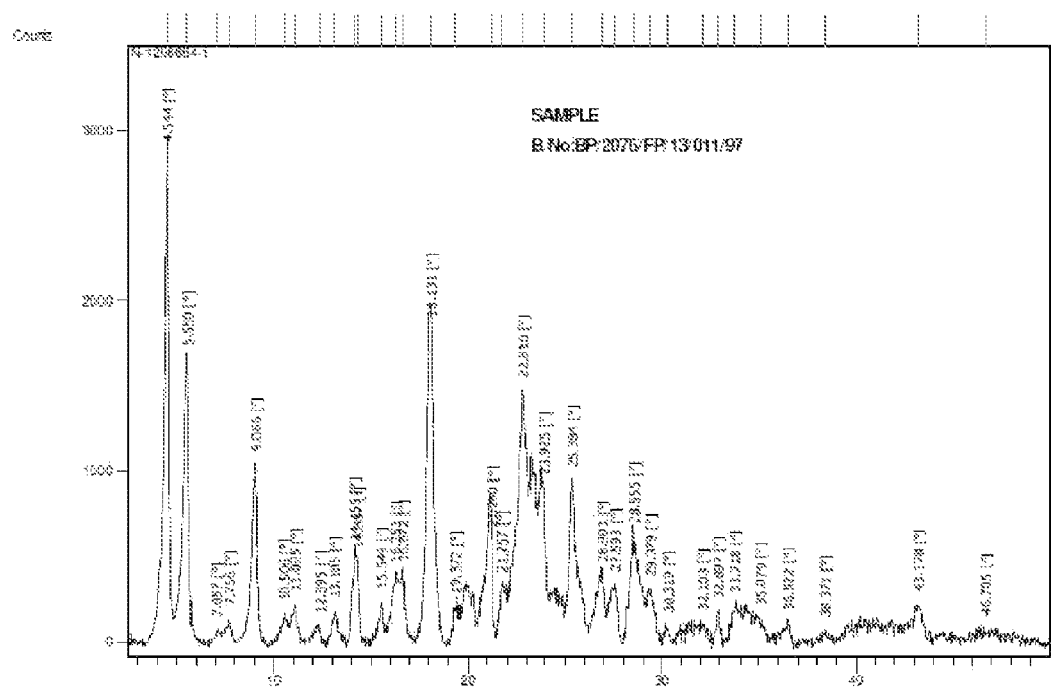
FIG. 1 represents X-ray Diffraction spectrum of the propylene glycol solvate of Regadenoson

The compound (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Regadenoson) may be prepared by any conventional method known in the art or by the below represented Scheme-1 which was disclosed in applicant's Indian Patent Application No. 4486/CHE/2012 and is incorporated herein by reference.

This application disclosed preparing 2-chloro adenosine in two steps followed by coupling with pyrazole-2-carboxamide to obtain 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

Scheme 1

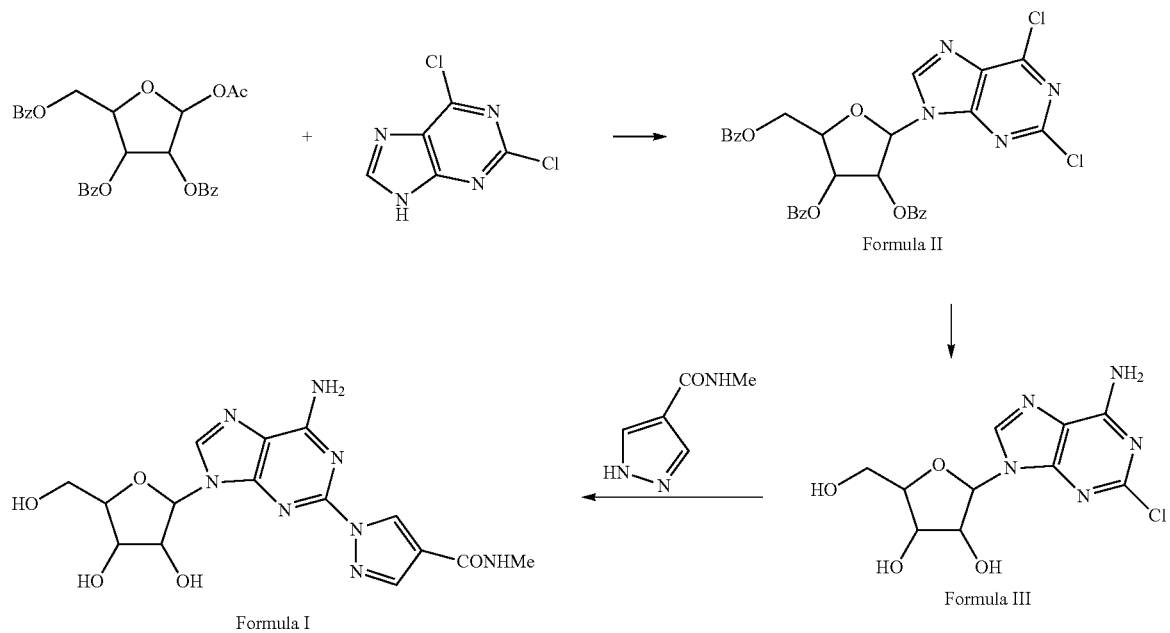

Preparation of Compound of Formula II

Preparation of compound of Formula II can be carried out in presence of a Lewis acid such as SnCl$_4$, TiCl$_4$, BBr$_3$, ZnCl, TMSOTf & and also other strong acids like H$_2$SO$_4$ & PTSA.

This reaction can be carried out in acetonitrile, EDC, DMF, DMA, and Toluene, preferably in EDC or in acetonitrile at 60-100° C. and alternatively the reaction can be carried out at 150-180° C. in absence of any solvents or lewis acid.

The product can be isolated as a pure anomer by dissolving the product in a suitable solvent, for example DMSO or protic solvents like MeOH, EtOH, IPA, t-Butanol & t-amyl alcohol. The product is also purified by dissolving the compound in protic solvents, addition of purified water and filtering the slurry that formed & washing the solid with water followed by ethanol and drying the solid that remains under vacuum at a temperature that does not exceed 50° C.

Preparation of Compound of Formula III

The compound of Formula III is prepared by reaction of Formula II with methanolic ammonia at room temperature in a sealed pressure reactor.

Preparation of Compound of Formula I

According to one aspect of the invention, the preparation of compound of Formula I can be carried out under basic conditions in presence of potassium carbonate, cesium carbonate, sodium hydroxide, potassium hydroxide, sodium bicarbonate, sodium methoxide, sodium ethoxide & potassium tertiary butoxide and preferably in presence of cesium carbonate at temperature of 25-150° C.

In another embodiment, preparation of compound of Formula I can be carried out with metal hydrides like sodium hydride, potassium hydride & calcium hydride.

This reaction can be carried out in toluene, t-amyl alcohol, NMP, DMA, DMF & DMSO. Preferably in NMP or DMA.

A further aspect of the invention is the coupling reaction which may require a copper catalyst in the reaction preferably copper iodide where such use increases the compound purity & yield as well, which was an aspect of previous inventions to obtain (1-{9-[(4S,2R, 3R,5R)-3,4-dihydroxy-5-(hydroxymethyl)oxolan-2-yl)-6-aminopurin-2-yl}pyrazole-4-yl)-N-methylcarboxamide.

Purification Process of Regadenoson and Preparation of Novel Polymorph of Regadenoson The crude Regadenoson obtained by any conventional method known in the art or by the method described herein above, was re-crystallized from propylene glycol to provide a highly pure compound.

Alternatively a co-solvent was added to aid the filtration of the solid from propylene glycol. The solvent was selected from THF, acetone, acetonitrile, toluene, ketone solvents, or alcohol solvents.

The process of preparing propylene glycol solvate of Regadenoson comprises following steps:
a). dissolving crude Regadenoson in propylene glycol;
b). heating the mass to 75-80° C. to obtain clear solution;
c). cooling the solution to 20-25° C.;
d). optionally adding an anti-solvent to the solution;
e). filtering the solid that separated out.

Figure 2:
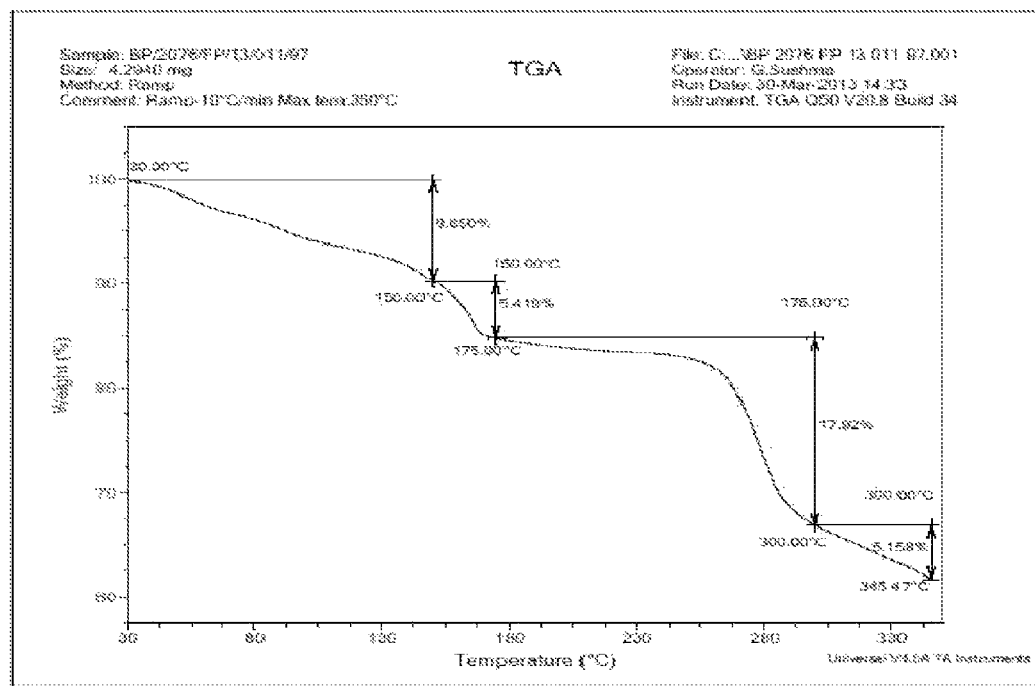
FIG. 2 represents TGA of the propylene glycol solvate of Regadenoson

The product obtained by the above process exhibits novel XRD characteristics and is obtained as a propylene glycol solvate of Regadenoson. The XRD and TGA are shown in the FIGS. 1-2. The novel propylene glycol solvate of Regadenoson is characterized by X-ray powder diffraction spectrum having principal peaks at 9.1, 18.0, 22.8 and 25.5 degrees 2 theta as illustrated in FIG. 1.

EXAMPLES

Example I 2,6-Dichloro-9-beta-D-(2,3,5-tri-O-benzoyl)-ribo-furanosylpurine (Formula II)

10.7 g of 2,6-dichloropurine and 30 g of 1-O-acetyl-2,3, 5-tri-O-benzoyl-beta-D-ribose were combined and heated to 100° C. with stirring to produce heterogeneous suspension. The reaction was allowed to stir at the same temperature until it became clear. The reaction was cooled and HOAc was removed under vacuum. Ethanol was added to the reaction and the solid isolated by filtration yielded 32 g of the crude product. The crude product was recrystallized from t-butanol to yield 28 g of 2,6-Dichloro-9-beta-D-(2,3, 5-tri-O-benzoyl)-ribofuranosylpurine.

Example 11

2-Chloro-9-(beta-D-ribofuranosyl)adenine (Formula III)

A solution of Formula II (30 g) in 600 mL of methanolic ammonia was heated in an autoclave at 100° C. for 24 hours. The solution was evaporated to dryness and codistilled with methanol to remove ammonia. The residue was recrystallized from Acetone. The product was dried in vacuo at 50° C. for 12 hours to yield 14 g of 2-Chloro-9-(beta-D-ribofuranosyl)adenine as a solid.

Example III

Method A

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in NMP is treated with potassium carbonate (1.5 eq) in a sealed reactor under an inert atmosphere. The mixture is heated at 100-150° C. for five hours and then diluted with aqueous HCl. Purification of the crude mixture by column chromatography to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide. The product was further purified by recrystallization from methanol to provide a pure compound.

Method B

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in xylene is treated with cesium carbonate (1.6 eq) in a sealed reactor under an inert atmosphere. The mixture is refluxed for 18 hours and then slurrying the crude mixture in acetonitrile to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide. The product was further recrystallized from IPA to provide a pure compound.

Method C

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in DMF is treated with sodium hydride (2 eq) in a sealed reactor under an inert atmosphere. The mixture is refluxed for 10 hours and then slurrying the crude mixture in acetone to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

Method D

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in xylene is treated with potassium carbonate (1.5 eq) followed by copper in a sealed reactor under an inert atmosphere. The mixture is refluxed for two hours and then diluted with aqueous HCl. Purification of the crude mixture by column chromatography to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

The product was further purified by recrystallization from ethanol or methanol/water mixture to provide a pure compound of >99.5%.

Method E

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in DMF is treated with cesium carbonate (1.6 eq) followed by CuI in a sealed reactor under an inert atmosphere. The mixture is refluxed for 30 minutes and then slurrying the crude mixture in acetonitrile to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide. The product was further purified from DMA to provide a pure compound. The compound was recrystallized in methanol water mixtures to provide a product of >99.5% purity.

Method F

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in DMAC is treated with cesium carbonate (2 eq) in a round bottom flask at 80-100° C. under an inert atmosphere. The reaction was heated for 6-10 hours and then the solvent distilled off. The mass was stirred in acetonitrile followed by methanol. And the methanol was distilled off to obtain a crude product. The crude regadenoson was recrystallized from acetonitrile and water. The solid obtained was azeotropically distilled to remove water completely and then dissolved in 7 vol of propylene glycol and heated to 75-80° C. to obtain a clear solution. The reaction is gradually cooled to 20-25° C. and allowed to stir for 12-15 h to obtain a solid. To the reaction is charged acetonitrile and the mass filtered. The solid obtained is again dissolved in 7 vol of propylene glycol and heated to dissolve at 75-80° C. The mass is cooled to 20-25° C. and stirred for 1-3 h and acetonitrile is added to the mass and filtered. The solid obtained is dried to give a propylene glycol solvate of 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide. The compound obtained by this process was >99.7% pure.

Method G

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in DMAC is treated with cesium carbonate (2 eq) in a round bottom flask at 80-100° C. under an inert atmosphere. The reaction was heated for 6-10 hours and then the solvent distilled off. The mass was stirred in acetonitrile followed by methanol. And the methanol was distilled off to obtain a crude product. The crude regadenoson was recrystallized from acetonitrile and water. The solid obtained was azeotropically distilled to remove water completely and then dissolved in 7 vol of propylene glycol and heated to 75-80° C. to obtain a clear solution. The reaction is gradually cooled to 20-25° C. and allowed to stir for 12-15 h to obtain a solid. To the reaction is charged THF and the mass filtered. The solid obtained is again dissolved in 7 vol of propylene glycol and heated to dissolve at 75-80° C. The mass is cooled to 20-25° C. and stirred for 1-3 h and THF is added to the mass and filtered. The solid obtained is dried to give a propylene glycol solvate of 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

The compound obtained by this process was >99.7% pure.

The obtained propylene glycol solvate of Regadenoson is characterized by X-ray powder diffraction spectrum having principal peaks at 9.1, 18.0, 22.8 and 25.5 degrees 2 theta as illustrated in FIG. 1.

We claim:

1. A propylene glycol solvate of Regadenoson.

2. The propylene glycol solvate of Regadenoson as claimed in claim 1, characterized by X-ray Powder Diffraction spectrum having principal peaks at 9.1, 18.0, 22.8 and 25.5 degrees 2 theta.

3. A process for the preparation of propylene glycol solvate of Regadenoson comprising the steps of:
 a) dissolving crude Regadenoson in propylene glycol;
 b) heating the mass to 75-80° C. to obtain clear solution;
 c) cooling the solution to 20-25° C.;
 d) optionally adding an anti-solvent to the solution; and
 e) filtering the solid that separated out.

4. The process as claimed in claim 3, wherein the anti solvent employed is selected from THF, acetonitrile, toluene, ketones or alcohols.

5. A process for preparation of propylene glycol solvate of Regadenoson characterized by X-ray Diffraction spectrum having principal peaks at 9.1, 18.0, 22.8 and 25.5 degrees 2 theta, comprising the steps of:
 a) dissolving crude Regadenoson in propylene glycol;
 b) heating the mass to 75-80° C. to obtain clear solution;
 c) cooling the solution to 20-25° C.;
 d) optionally adding an anti-solvent to the solution; and
 e) filtering the solid that separated out.

6. The process as claimed in claim 5, wherein the anti solvent employed is selected from THF, acetonitrile, toluene, ketones or alcohols.

* * * * *